United States Patent [19]

Tsukashima et al.

[11] Patent Number: 5,458,639
[45] Date of Patent: Oct. 17, 1995

[54] CATHETER BALLOON DISTAL BOND

[75] Inventors: Ross Tsukashima; Karen M. Rowean; Morris H. Dietermann, all of San Diego, Calif.

[73] Assignee: Medtronic, Inc., Minneapolis, Minn.

[21] Appl. No.: 286,815

[22] Filed: Aug. 5, 1994

[51] Int. Cl.$^6$ .................................. A61M 29/00
[52] U.S. Cl. ............................ 604/97; 604/96; 606/192
[58] Field of Search .................... 604/53, 55, 96, 604/97, 98, 280, 282, 283; 606/192, 194; 128/662.06

[56] References Cited

U.S. PATENT DOCUMENTS

| | | | |
|---|---|---|---|
| 4,723,936 | 2/1988 | Buchbinder | 604/95 |
| 4,748,982 | 6/1988 | Horzewski | 128/344 |
| 4,762,129 | 8/1988 | Bonzel | 128/344 |
| 4,782,834 | 11/1988 | Maguire | 128/344 |
| 4,790,315 | 12/1988 | Mueller, Jr. | 128/344 |
| 4,917,666 | 4/1990 | Solar et al. | 604/95 |
| 4,928,693 | 5/1990 | Goodin et al. | 128/637 |
| 4,947,864 | 8/1990 | Schockey et al. | 128/772 |
| 4,988,356 | 1/1991 | Crittenden | 606/192 |
| 5,040,548 | 8/1991 | Yock | 128/898 |
| 5,057,120 | 10/1991 | Farcot | 606/194 |
| 5,061,273 | 10/1991 | Yock | 606/194 |
| 5,108,525 | 4/1992 | Gharibadeh | 156/86 |
| 5,135,535 | 8/1992 | Kramer | 606/194 |
| 5,154,725 | 10/1992 | Leopold | 606/194 |
| 5,156,594 | 10/1992 | Keith | 604/96 |
| 5,156,595 | 10/1992 | Adams | 604/96 |
| 5,180,367 | 1/1993 | Kontos et al. | 604/101 |
| 5,232,445 | 8/1993 | Bonzel | 604/96 |
| 5,277,199 | 1/1994 | DuBois et al. | 128/772 |
| 5,290,230 | 3/1994 | Ainsworth | 604/96 |
| 5,324,257 | 6/1994 | Osborne et al. | 604/53 |
| 5,328,472 | 7/1994 | Steinke | 604/96 |
| 5,330,444 | 7/1994 | Webler et al. | 604/265 |
| 5,334,154 | 8/1994 | Samson et al. | 604/102 |

FOREIGN PATENT DOCUMENTS

| | | |
|---|---|---|
| 9411053 | 5/1994 | WIPO . |
| 9411048 | 5/1994 | WIPO . |

Primary Examiner—C. Fred Rosenbaum
Assistant Examiner—Bryan L. Tsosie
Attorney, Agent, or Firm—Dianne M. F. Plunkett; Harold R. Patton

[57] ABSTRACT

The present invention is accomplished by providing a catheter with a shaft having a balloon affixed to the distal end, a core wire extending throughout the shaft and throughout the balloon, the core wire having a tube surrounding the distal end, a sleeve defining a guidewire lumen extending parallel, and exterior to the shaft and to the exterior to the balloon. In yet another embodiment the catheter shaft has a balloon affixed to the distal end and a sleeve defining a guidewire lumen extending parallel and exterior to the shaft and to the balloon exterior. In yet another embodiment the catheter shaft has a balloon affixed to the distal end and a core wire extending throughout the shaft and throughout the balloon with the core wire having a tube surrounding the distal end. In each embodiment the balloon is compressed to itself to form a compressed area just distal to the distal balloon cone for separating the balloon inflation lumen from a sleeve lumen. A skive is cut in the balloon just distal to the compressed area to form a proximal port for the sleeve lumen. In the embodiment with a sleeve, the sleeve is affixed to the shaft and balloon as well as the sleeve extending through the sleeve lumen within which the sleeve is affixed.

20 Claims, 4 Drawing Sheets

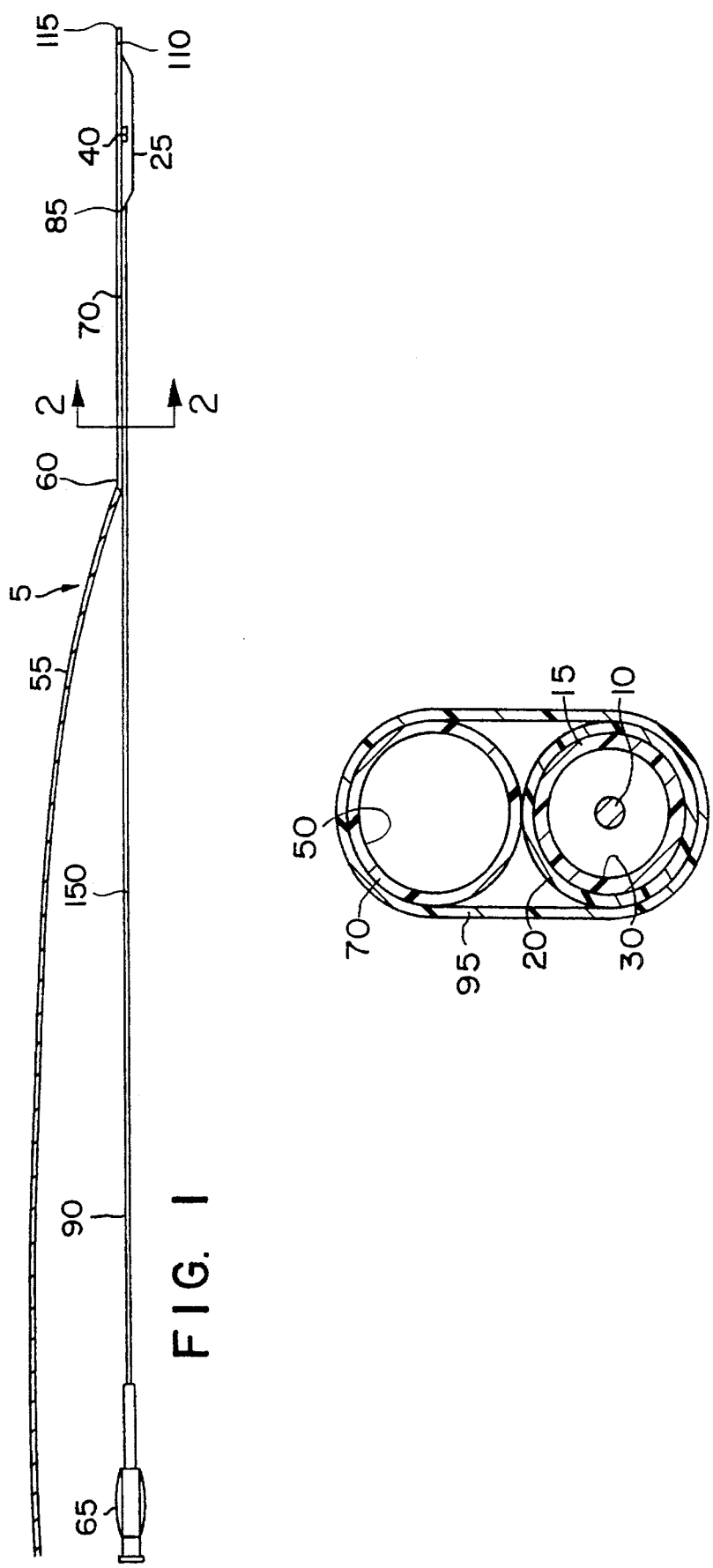

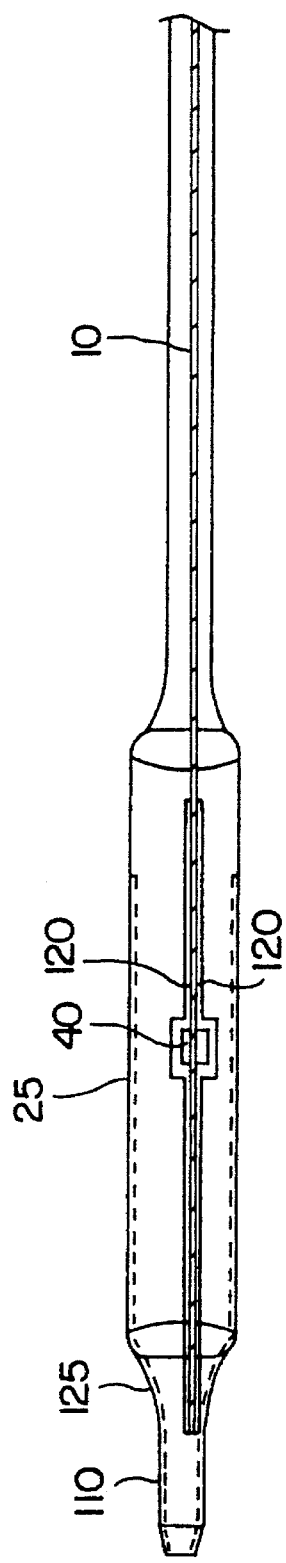
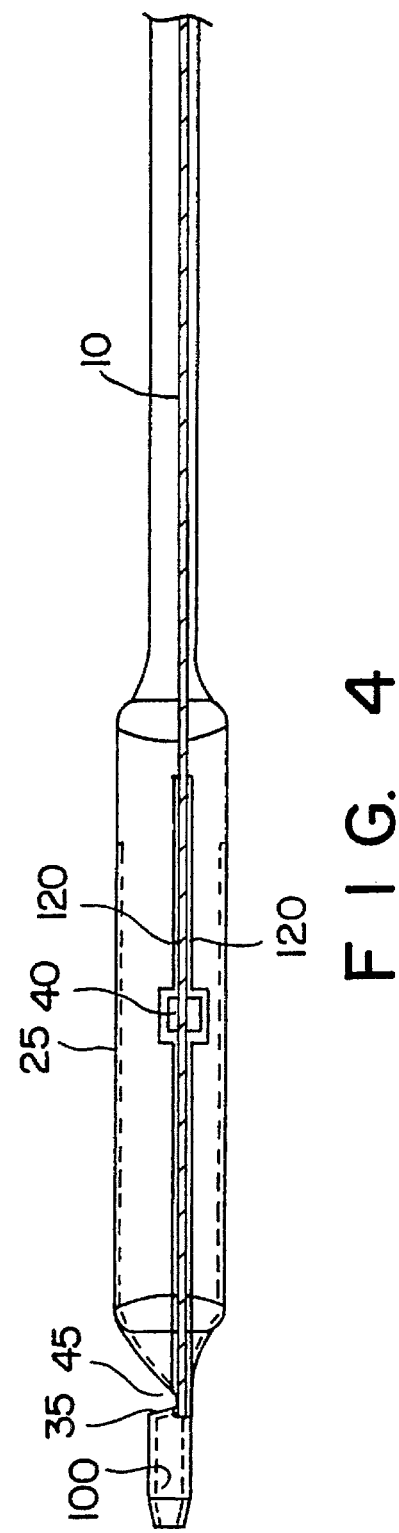

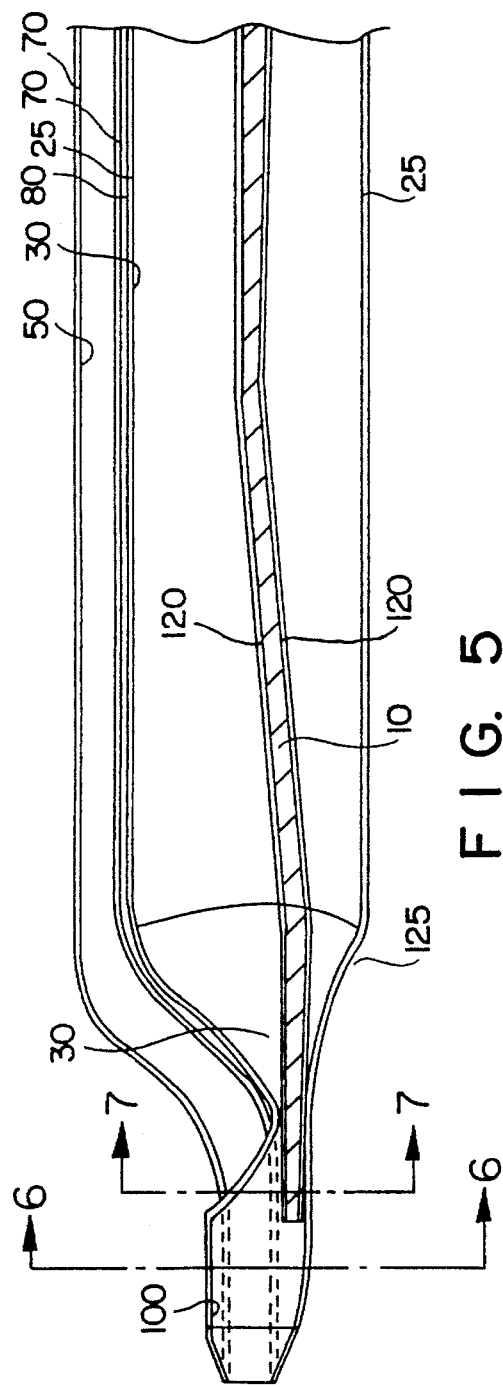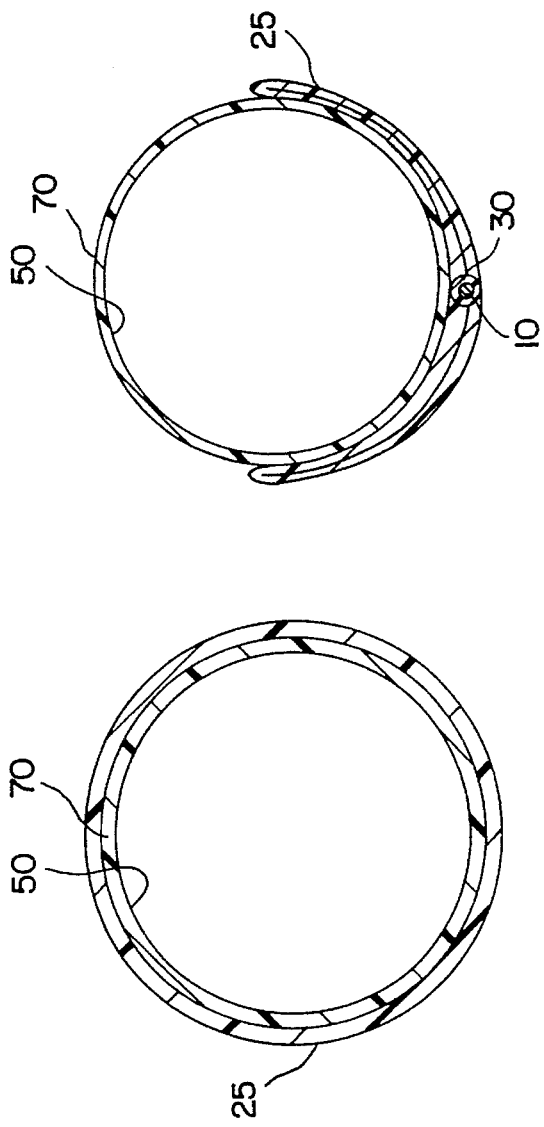

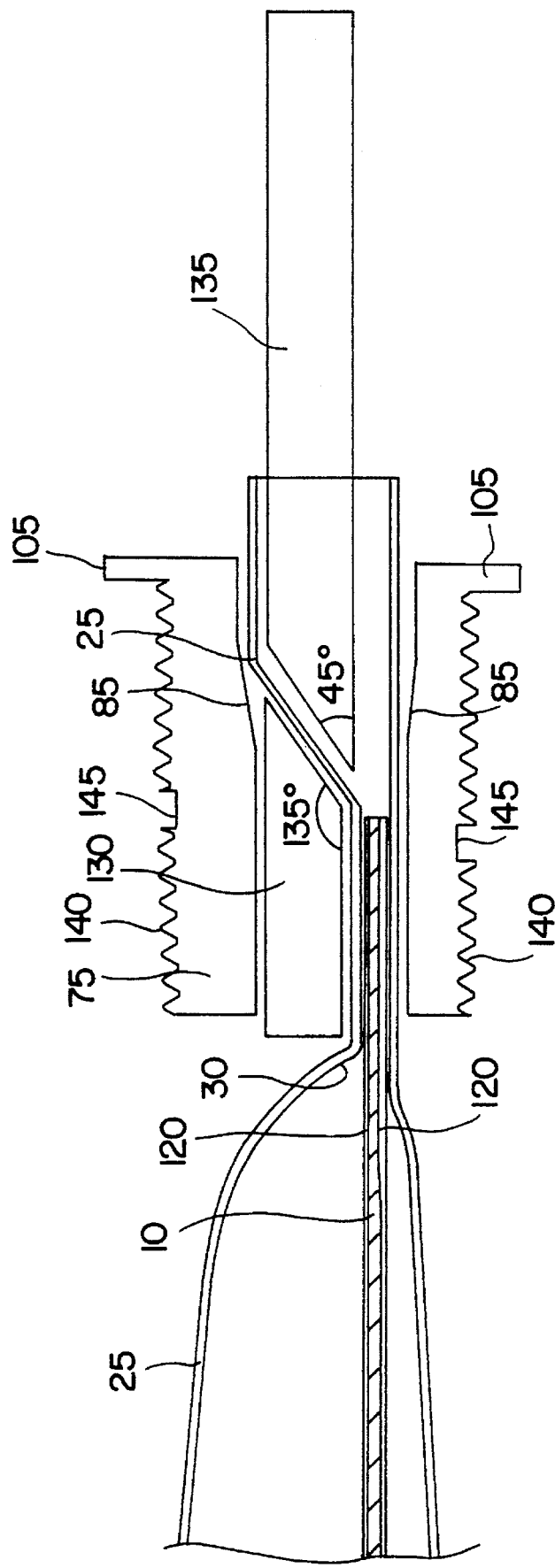

CATHETER BALLOON DISTAL BOND

FIELD OF THE INVENTION

The present invention relates to angioplasty catheters and more particularly, to a distal balloon bond.

BACKGROUND OF THE INVENTION

Catheters are tube-like members inserted into the body for diagnostic or therapeutic reasons. One of the therapeutic procedures applicable to the present invention is known as percutaneous transluminal coronary angioplasty (PTCA). This procedure can be used, for example, to reduce arterial build-up of cholesterol fats or atherosclerotic plaque. Using a movable wire system, one could more readily select the desired coronary artery and reach smaller branches as movable guidewires are smaller and more flexible than the fixed wire systems. The catheter is subsequently tracked over the guidewire to the stenosis. The balloon at the distal end of the catheter is then inflated causing the site of the stenosis to widen. After the balloon is deflated, the catheter is withdrawn over the guidewire and another catheter can be slid into place over it if necessary.

Various versions of rapid exchange catheters, either coaxial or biaxial, are shown in the following patents: U.S. Pat. Nos. 4,762,129 and 5,232,445 issued to Bonzel, U.S. Pat. Nos. 5,040,548 and 5,061,273 issued to Yock, U.S. Pat. No. 4,748,982 issued to Horzewski, et at., U.S. Pat. No. 4,988,356 issued to Crittenden, U.S. Pat. No. 5,135,535 issued to Kramer; U.S. Pat .No. 5,180,367 to Kontos; assignee's WO 94/11048 issued to Jung et at.; assignee's WO 94/11053 issued to Ndondo-Lay et at.; and assignee's copending application 08/149,887 to Khairkhahan et at.

The following are examples of spring coil catheters. Some catheters, such as the present assignee's 14K™ catheter and Thruflex® catheter to Solar and Roucher (shown in U.S. Pat. No. 4,917,666) are over-the-wire catheters having spring coil lumens to improve the pushability of the catheter. At the same time, the spring coil is flexible laterally, with minimized kinking. In the present assignee's Gold X™ catheter, a coaxial rapid exchange catheter shown in U.S. Pat. No. 5,328,472 issued Jul. 12, 1994 to Steinke et al., the outer lumen is similarly made of a spring coil, with a core wire extending through a portion of the coil for added pushability. In the present assignee's Omniflex™ catheter to Buchbinder and Solar (shown generally in U.S. Pat. No. 4,723,936) as sold, a proximal hypotube about 3.81 cm (1.50 inches) long improves the handling of the catheter, which is otherwise formed of a spring coil.

The following illustrates distal balloon bonds used in the prior art. Adhesives are used in U.S. Pat. No. 4,748,982 to Horzewski et al. (col. 3, lines 18–27); in U.S. Pat. No. 4,782,834 to Maguire et al. (col. 3, lines 50–53); in U.S. Pat. No. 5,154,725 to Leopold (cyanoacrylate such as Loctite™ 404, col. 5, lines 6–8); in U.S. Pat. No. 5,156,594 to Keith (Epoxy or cyanoacrylate, col. 8 lines 21–24); in U.S. Pat. No. 5,156,595 to Adams (Epoxy, col. 3, lines 37–41); and in U.S. Pat. No. 5,290,230 to Ainsworth et al. (col. 6, lines 27–30).

Heat shrinking is used in U.S. Pat. No. 4,748,982 to Horzewski et al. (col. 3, lines 22–27). Necking down is used in U.S. Pat. No. 4,790,315 to Mueller et al. (col. 4, claim 7). Bonding is used in U.S. Pat. No. 5,061,273 to Yock (col. 2, lines 55–58). A bonded twisted section is used in U.S. Pat. No. 5,108,525 to Gharibadeh (col. 4, lines 12–19).

What is needed is a method of attaching the distal end of a balloon which is reliable and minimizes the distal bond profile.

SUMMARY OF THE INVENTION

The present invention is accomplished by providing a catheter with a shaft having a balloon affixed to the distal end, a core wire extending throughout the shaft and throughout the balloon, the core wire having a tube surrounding the distal end, a sleeve defining a guidewire lumen extending parallel, and exterior to the shaft and to the exterior to the balloon. In yet another embodiment the catheter shaft has a balloon affixed to the distal end and a sleeve defining a guidewire lumen extending parallel and exterior to the shaft and to the balloon exterior. In yet another embodiment the catheter shaft has a balloon affixed to the distal end and a core wire extending throughout the shaft and throughout the balloon with the core wire having a robe surrounding the distal end. In each embodiment the balloon is compressed to itself to form a compressed area just distal to the distal balloon cone for separating the balloon inflation lumen from a sleeve lumen. A skive is cut in the balloon just distal to the compressed area to form a proximal port for the sleeve lumen. In the embodiment with a sleeve, the sleeve is affixed to the shaft and balloon as well as the sleeve extending through the sleeve lumen within which the sleeve is affixed.

It is desirable that balloon bonds not increase the outer diameter of the catheter shaft or manufacturing time. Adhesives increase shaft diameter and adhesive curing time increases manufacturing time. One part ultraviolet light cure adhesives cure rapidly in about 15 seconds under exposure to ultraviolet light. These are undesirable because they result in a larger profile then does a heat bond. One part ultraviolet cure adhesives can also damage the balloon and may require treating the balloon interior with plasma. Cyanoacrylate and Loctite™ 404 are examples of one part adhesives. Two part adhesives do not require plasma treatment and therefore may not result in deterioration of the balloon interior but do result in a larger profile than does a heat bond. Two part adhesives furthermore increase manufacturing time because of the additional mixing time required as well as the very long curing times required. Epoxy is an example of a two part adhesive. Applicant's proximal bond avoids the use of adhesives resulting in reduced profile and reduced manufacturing time.

BRIEF DESCRIPTION OF THE DRAWINGS

FIG. 1 is a side elevational view;

FIG. 2 is a cross-sectional view taken along the line 2—2 in FIG. 1;

FIG. 3 is a longitudinal view of the area of the balloon area before heat bonding;

FIG. 4 is a longitudinal view of the balloon after heat bonding and skiving;

FIG. 5 depicts a longitudinal cross-section of the distal bond area;

FIG. 6 is a cross-sectional view taken along the line 6—6 in FIG. 5;

FIG. 7 is a cross-sectional view taken along the line 7—7 in FIG. 5 with the uninflated, folded balloon; and FIG. 8 is a longitudinal cross-section of the left and right forming pins inserted in a balloon and the balloon within a die.

DETAILED DESCRIPTION OF THE PREFERRED EMBODIMENTS

Although a specific biaxial lumen, rapid exchange, spring coil shaft with a core wire will be described herein as seen in FIG. 1, it is understood that the Applicant's distal bond invention could be used with other forms of catheter shaft technology such as a coaxial lumen shaft or nonspring coil shaft.

The distal bond 45 is formed into a unique U-shape enabling the distal portion of the balloon 25 to be attached easily to the sleeve 70. FIG. 3 illustrates the distal tip 110 of a typical balloon catheter 5. A metal corewire 10 is shown inside the balloon 25. The distal neck of the balloon 25 is compressed so that the balloon 25 is completely sealed off. This results in the distal tip of the corewire 10 becoming anchored inside the compressed area. FIG. 4 illustrates a skive 35 cut in the distal neck of the balloon 25 to reopen the sleeve lumen 100.

FIG. 5 shows the completed assembly after the sleeve 70 is inserted into the skive 35 and through the sleeve lumen 100 where it is bonded in place. The FIG. 6 cross-section illustrates the balloon 25 distal neck when bonded coaxially to the outer diameter of the sleeve 70. The FIG. 7 cross-section illustrates a cross-section of the distal bond 45 site with the corewire 10 embedded within.

The advantages of the distal bond 45 design are as follows. The U-shaped bond forms a natural cradle in which the sleeve 70 for the guidewire 55 nests resulting in ease of assembly. Applicant's design minimizes the distal bond 45 profile. Increased distal bond 45 strength is achieved as compared to adhesives due to the compression applied during formation. Anchoring the corewire 10 within the distal bond 45 increases the amount of energy that can be transmitted to the distal tip 110 during catheter 5 advancement. The bonded core wire 10 at the distal tip 110 improves pushability. Bond performance is more consistent and yield is higher when compared to adhesive bonds.

Referring to FIGS. 1 through 8, a preferred rapid exchange catheter 5 according to the present invention is formed of a shaft, an external guidewire lumen 50 defined by sleeve 70 and also balloon 25. The shaft comprises a hypotube 90 at the proximal end of the shaft which is affixed to the FIG. 2 spring coil 15 comprising the distal end of the shaft. The spring coil 15, has a jacket 20 surrounding the coil. The jacket 20 defines the balloon inflation lumen 30. The balloon is preferably made of irradiated Low Density Polyethylene (LDPE). At the proximal end, a handle 65 is attached to the hypotube 90.

The hypotube 90 of FIG. 1 extends at least half the length of the shaft, preferably about two-thirds of the length of the shaft, and the spring coil 15 forms the remainder of the shaft. In the preferred embodiment, the catheter is about 135 cm (53.15 inches) long and the hypotube 90 extends through the proximal 98 cm. The spring coil 15 is sealed and jacketed 20 with polyethylene so that it forms an inflation lumen 30. The stainless steel hypotube 90, is coated for lubricity resulting in a 1.8 fr diameter of 0.6 min. Coating agents such as fluoropolymers may be used.

The optional FIG. 2 spring coil 15 is approximately 32.5 cm long and has a shaft diameter of 2.2 fr (0.7 mm). The external lumen jacket 95 which encloses both the sleeve 70 and the spring coil 15 has a 3.0 fr shaft outer diameter of 1.2 mm. The spring coil 15 can be brazed 150 to the distal end of hypotube 90 and extends to the proximal end of balloon 25. Spring coil 15 is a helically wound flat wire preferably made of a biocompatible material such as stainless steel or tungsten and, together with the hypotube, renders the catheter highly pushable. A further advantage of a metal spring coil 15 is that it is visible under fluoroscopy, thereby serving as a proximal balloon 100 marker.

Jacket 20 of FIG. 2 covering spring coil 15 consists of a biocompatible thermoplastic such as polyethylene or polyester. The thermoplastic may be optionally irradiated. Irradiation renders materials easier to neck down and permits greater exposure to heat without breakage. When using a spring coil shaft, irradiation is necessary because it renders the jacket 20 distendable such that it will fit over the spring coil 15 prior to being heat shrunk about the spring coil 15. Jacket 20 is heat shrunk at its proximal end to the distal end of hypotube 90 and over the proximal end of spring coil 15.

The balloon 25 is preferably made of a non-compliant biocompatible material such as polyethylene and is in fluid communication with the inflation lumen 30 which is used to transmit fluids therethrough for purposes of inflating the balloon 25 and reducing the stenosis. The proximal end of the balloon 25 is affixed to the distal end of the jacket 20.

An optional core wire 10 of FIGS. 2, 3, 4, 5, 7 and 8 can be attached to hypotube 90 and extends through spring coil 15 and through balloon 25 to the distal end of the catheter to improve pushability and provide added support to the catheter and balloon. Core wire 10 is tapered along its length, from a diameter of about 0.030 cm (0.012 inches) to about 0.010 cm (0.004 inches). Core wire 10 provides stiffness which improves pushability and torquability. In some embodiments the catheter materials are stiff enough to provide sufficient pushability alone, as may be the case with high density polyethylene or polyester. FIG. 2 shows the core wire 10 as being centered within the balloon inflation lumen 30. Those skilled in the art will understand that the core wire 10 moves about within the balloon inflation lumen 30 such that it is not always centered given slacking and bending.

As seen in FIGS. 1, 3, and 4, a radiopaque marker band 40 is bonded to core wire 10 preferably at the center of the balloon 25. The marker band 40 is used to fluoroscopically view the position of the balloon 25 during dilatation to assist the physician in accurately locating the balloon with respect to the shape or morphology of the lesion. Preferred materials for the marker band 40 include gold or platinum or iridium and alloys of these materials such as 90% platinum and 10% iridium. The distal portion of the spring coil 15 may also be fabricated of a radiopaque material such as platinum to make it visible under a fluoroscope. In some embodiments, the marker band 40 may be eliminated and the entire spring coil 15, or just the distal end of the spring coil 15, may be made of radiopaque materials as described above.

Extending generally parallel to the catheter 5 and exterior to balloon 25 is external guidewire lumen 50 which is defined by sleeve 70 as seen in FIGS. 1 and 5. Sleeve 70 originates proximal to the balloon 25 and continues to the distal end of the catheter forming the distal tip 110. Sleeve 70 slidably receives and directs guidewire 55 during use, the guidewire passing through proximal port 60, through the sleeve and through distal port 115. The sleeve 70 surrounding the external guidewire lumen 50 is laminated to the inflation lumen jacket 20 and adhesively bonded to balloon 25 with an adhesive 80 such as a UV cure Loctite™ 3321. The sleeve 70 is placed over the jacket 20 and balloon 25 and then the distal end of the sleeve 70 is threaded through the sleeve lumen 100 before the laminate, preferably low or high density polyethylene, is heat shrunk around sleeve 70. The external lumen jacket 95 ends approximately at the distal end of the spring coil 15.

When the catheter is used as a rapid exchange catheter, sleeve 70 is preferably either about 7 cm (2.76 inches) long or about 20 cm (7.87 inches) long. The sleeve can be made of high density polyethylene, polyimide, polyester or nylon, and is preferably polyethylene. A mandrel is placed within the sleeve 70 during the manufacturing process to maintain the shape and to maintain the proximal port 60. The shorter guidewire lumen promotes easy exchange of the catheter.

A variety of FIG. 1 guidewire 55 sizes can be used with applicant's invention. The guidewire size dictates the inner diameter of sleeve 70. The sleeve 70 inner diameter must be larger than the outer diameter of the guidewire. For example, when a 0.036 cm (0.014 inches) guidewire is used the inner diameter for sleeve 70 should preferably be about 0.043 cm (0.017 inches), and the outer diameter should be preferably about 0.053 cm (0.021 inches). For a 0.025 cm (0.010 inches) guidewire, the inner diameter may be about 0.033 cm (0.013 inches) and the outer diameter about 0.046 cm (0.018 inches).

The distal end of the core wire 15 to just proximal of the marker band 40 are enclosed in an irradiated tubing 120 of FIGS. 3, 4, 5, and 8 such as polyethylene or polyester by means of heat shrinking to prevent the marker band 40 from damaging the balloon. The optional irradiation makes bonding the distal end of the balloon to the core wire 15 easier. Irradiating the polyethylene gives the tubing better shape memory.

The balloon distal bond 45 is formed using a heat bonding process as follows. A left forming pin 130 and a right forming pin 135 can be used as shown in FIG. 8. The left 130 and right 135 forming pins are preferably cylindrical in shape and are cut at complimentary angles and are positioned approximately 0.5 mm apart between the angled ends. The left forming pin 130 seals the balloon inflation lumen 30 and the right forming pin 135 creates the sleeve lumen 100.

The right forming pin 135 is approximately 10.2 cm (4 inches) long, consisting of a 0.057 cm (0.0225 inch) diameter paralene coated mandrel which is cut on an angle at one end. The angle should be less than 90 degrees and more preferably, 45 degrees. This size forming pin 135 is suitable when creating sleeve lumens 100 for a 0.053 cm–0.056 cm (0.021 inch to 0.022 inch) guidewire outer diameter. The right forming pin 135 must be coated as it is the pin which will be inserted into the distal end of the balloon 25. Only about 1.27 cm (½ inch) to 2.54 cm (1 inch) of the right forming pin 135 will be in contact within the balloon.

The left forming pin 130 is an uncoated mandrel cut on a complimentary angle to that of the right forming pin's 135 angle. Thus, if the right forming pin 135 angle is 45 degrees, the angle of the left forming pin 130 will be 135 degrees. It is unnecessary to coat the left forming pin 130 as it will only be used on the surface of the bond. The left forming pin 130 is 3–5 mm long, having a diameter which can vary with the balloon size. For example, 2.0 mm balloons use a die 75 with a 0.081 cm (0.032 inch) inner diameter and a left forming pin 130 with a 0.066 cm (0.026 inch) diameter; 2.5 mm balloons use a die 75 with a 0.086 cm (0.034 inch) inner diameter and a left forming pin 130 with a 0.066 cm (0.026 inch) diameter; 3.0 mm balloons use a die 75 with a 0.091 cm (0.036 inch) inner diameter and a left forming pin 130 with a 0.058 cm (0.023 inch) diameter; 3.5 mm balloons use a die 75 with a 0.097 cm (0.038 inch) inner diameter and a left forming pin 130 with a 0.058 cm (0.023 inch) diameter; 4.0 mm balloons use a die 75 with a 0.101 cm (0.040 inch) inner diameter and a left forming pin 130 with a 0.058 cm (0.023 inch) diameter.

The distal bond 45 length should be a minimum of 0.5 mm. The core wire 10 should be positioned 1.0–2.0 mm past the balloon distal cone 125 such that the core wire 10 extends a minimum of 0.5 mm into the distal bond 45 without exceeding the distal bond 45 length. The tubing 120 is heat shrunk around the distal end of the core wire 10 to just proximal to the marker band 40. The tubing 120 is made of irradiated polyethylene. Slide the distal end 110 of the balloon 25 over the angled end of the right forming pin 135 until the tubing 120 is approximately 0.5 mm from the angled end of the right forming pin 135. The core wire 10 should be under the left forming pin 135. The balloon area distal to the distal balloon cone 125 is placed in a round disk shaped die 75. This will include the core wire 10, the tubing 120, the left forming pin 130 and the right forming pin 135.

The outer diameter of the die 75 has threads 140 which can be screwed into a heater coil. The die 75 has a flared area 85 for a loose fit over the distal end of the balloon 25. The die 75 also has a finger hold 105. A flattened area 145 on the die 75 is undercut to keep the die 75 from getting too hot.

Heat is maintained at the distal bond 45 for approximately 90 seconds at a temperature which varies with the size of the balloon. The die 75 temperature for 2.0 mm balloons should be 169° C., for 2.5 mm balloons it should be 170° C., for 3.0 mm balloons it should be 153° C., for 3.5 mm balloons it should be 156° C. and for 4.0 mm balloons it should be 160° C. The balloon should be allowed to cool to approximately 40° C., or approximately ambient temperature, before removing it from the die 75 to prevent damaging the balloon.

During the heating and cooling associated with this formation process, distal bond 45 should be kept under tension to prevent it from distorting. This can be done, for example, by placing a clamp over the distal end of the balloon 25 which protrudes beyond the distal end of the die 75. The amount of force necessary varies with the size of the balloon. For small balloons such as 2.0 mm, approximately 0.01 lbs of force is sufficient. Larger balloons such as 4.0 mm require approximately 0.25 lbs. of force.

A skive 35 is cut in the balloon just distal to the area of the balloon 25 which has just been compressed into the balloon by the right and left forming pins 135 and 130. The skive 35 forms a proximal entry port for the sleeve lumen 100. The compressed area is just distal to the distal balloon cone. Extending generally parallel to the catheter 5 and exterior to balloon 25 is external guidewire lumen 50 which is defined by sleeve 70 as seen in FIGS. 1 and 5. Sleeve 70 originates proximal to the balloon 25 and continues to the distal end of the catheter forming the distal tip 110. Sleeve 70 slidably receives and directs guidewire 55 during use, the guidewire passing through proximal port 60, through the sleeve and through distal port 115. The sleeve 70 surrounding the external guidewire lumen 50 is laminated to the inflation lumen jacket 20 and adhesively bonded to balloon 25 with an adhesive 80 such as a UV cure Loctite™ 3321. The sleeve 70 is placed over the jacket 20 and balloon 25. Next, the distal end of the sleeve 70 is threaded through, and affixed to the sleeve lumen 100 before the laminate, preferably low or high density polyethylene, which forms the external lumen jacket 95, is heat shrunk around sleeve 70. The external lumen jacket 95 ends approximately at the distal end of the spring coil 15. The sleeve lumen 100 has a distal end with an exit port 115 for the guidewire 55.

The preening specific embodiments are illustrative of the practice of the invention. It is to be understood, however, that other expedients known to those skilled in the art or

| No. | Component |
|---|---|
| 5 | Balloon Catheter |
| 10 | Core Wire |
| 15 | Spring Coil |
| 20 | Inflation Lumen Jacket |
| 25 | Balloon |
| 30 | Balloon Inflation Lumen |
| 35 | Skive |
| 40 | Radiopaque Marker Band |
| 45 | Distal Bond |
| 50 | External Guidewire Lumen |
| 55 | Guidewire |
| 60 | Proximal Port |
| 65 | Handle |
| 70 | Sleeve |
| 75 | Die |
| 80 | Adhesive |
| 85 | Flared Area |
| 90 | Hypotube |
| 95 | External Lumen Jacket |
| 100 | Lumen for Sleeve |
| 105 | Finger Hold |
| 110 | Distal Tip |
| 115 | Distal Port |
| 120 | Tubing |
| 125 | Distal Balloon Cone |
| 130 | Left Forming Pin |
| 135 | Right Forming Pin |
| 140 | Threads |
| 145 | Die Flattened Area |
| 150 | Braze |

What is claimed is:

1. A catheter comprising:

a longitudinally extending shaft having a distal end and a proximal end, the shaft defining an inflation lumen;

a balloon having a distal end and a proximal end, a distal cone and a proximal cone, the proximal end of the balloon being sealingly affixed to the distal end of the shaft, the balloon defining an inflation lumen in fluid communication with the shaft inflation lumen;

a core wire having a distal end and a proximal end, the core wire extending longitudinally through the shaft inflation lumen and the balloon inflation lumen to a point just proximal of the distal end of the balloon;

a longitudinally extending tube having a distal end and a proximal end, the tube defining a core wire lumen, the tube distal end is affixed to and surrounding the distal end of the core wire, the core wire extending longitudinally through the core wire lumen;

a sleeve having a distal end and a proximal end, the sleeve defining a guidewire lumen, the sleeve extending parallel, longitudinally and exterior to the shaft and balloon, the sleeve extending to the distal end of the balloon and terminating in a proximal port proximal to the balloon, the sleeve being affixed to the balloon;

the balloon being compressed to itself to form a compressed area distal to the distal balloon cone for separating the balloon inflation lumen from a sleeve lumen, the core wire being anchored inside the compressed area; and a skive being cut in the balloon just distal to the compressed area to form a proximal port for the sleeve lumen, the sleeve extending through the sleeve lumen, the sleeve lumen having a distal port and the distal end of the sleeve being affixed within the sleeve lumen.

2. A catheter according to claim 1 wherein the core wire extends approximately 1.0 to 2.0 mm distal to the balloon distal cone.

3. A catheter according to claim 1 wherein the tube is made of irradiated thermoplastic.

4. A catheter according to claim 1 wherein the core wire extends a minimum of 0.5 mm into the compressed area, and not exceeding the length of the compressed area.

5. A catheter according to claim 1 wherein the compressed area extends a minimum of 0.5 mm.

6. A catheter according to claim 1 wherein at least one marker band having a proximal end and a distal end is affixed to the core wire within the balloon, wherein the proximal end of the tube extends distal to the distal end of the marker band.

7. A catheter comprising:

a longitudinally extending shaft having a distal end and a proximal end, the shaft defining an inflation lumen;

a balloon having a distal end and a proximal end, a distal cone and a proximal cone, the proximal end of the balloon being sealingly affixed to the distal end of the shaft, the balloon defining an inflation lumen in fluid communication with the shaft inflation lumen;

a sleeve having a distal end and a proximal end, the sleeve defining a guidewire lumen, the sleeve extending parallel, longitudinally and exterior to the shaft and balloon, the sleeve extending to the distal end of the balloon and terminating in a proximal port proximal to the balloon, the sleeve being affixed to the balloon;

the balloon being compressed to itself to form a compressed area distal to the distal balloon cone for separating the balloon inflation lumen from a sleeve lumen; and a skive being cut in the balloon just distal to the compressed area to form a proximal port for the sleeve lumen, the sleeve extending through the sleeve lumen, the sleeve lumen having a distal port and the distal end of the sleeve being affixed within the sleeve lumen.

8. A catheter according to claim 7 wherein the compressed area extends a minimum of 0.5 mm.

9. A catheter according to claim 7 further comprising:

a core wire having a distal end and a proximal end, the core wire extending longitudinally through the shaft inflation lumen and the balloon inflation lumen to a point just proximal of the distal end of the balloon, the core wire being anchored inside the compressed area; and a longitudinally extending tube having a distal end and a proximal end, the tube defining a core wire lumen, the tube distal end affixed to and surrounding the distal end of the core wire, the core wire extending longitudinally through the core wire lumen.

10. A catheter according to claim 9 wherein the core wire extends approximately 1.0 to 2.0 mm distal to the balloon distal cone.

11. A catheter according to claim 9 wherein the tube is made of irradiated thermoplastic.

12. A catheter according to claim 9 wherein the core wire extends a minimum of 0.5 mm into the compressed area, and not exceeding the length of the compressed area.

13. A catheter according to claim 9 wherein at least one marker band having a proximal end and a distal end is affixed to the core wire within the balloon, wherein the proximal end of the tube extends distal to the distal end of the marker band.

14. A catheter comprising:

a longitudinally extending shaft having a distal end and a proximal end, the shaft defining an inflation lumen;

a balloon having a distal end and a proximal end, a distal cone and a proximal cone, the proximal end of the balloon being sealingly affixed to the distal end of the shaft, the balloon defining an inflation lumen in fluid communication with the shaft inflation lumen;

a core wire having a distal end and a proximal end, the core wire extending longitudinally through the shaft inflation lumen and the balloon inflation lumen to a point just proximal of the distal end of the balloon;

a longitudinally extending tube having a distal end and a proximal end, the tube defining a core wire lumen, the tube distal end is affixed to and surrounding the distal end of the core wire, the core wire extending longitudinally through the core wire lumen;

the balloon being compressed to itself to form a compressed area distal to the distal balloon cone for separating the balloon inflation lumen from a sleeve lumen, the core wire being anchored inside the compressed area; and a skive being cut in the balloon just distal to the compressed area to form a proximal port for the sleeve lumen, the sleeve lumen having a distal port.

15. A catheter according to claim 14 further comprising:

a sleeve having a distal end and a proximal end, the sleeve defining a guidewire lumen, the sleeve extending parallel, longitudinally and exterior to the shaft and balloon, the sleeve extending to the distal end of the balloon and terminating in a proximal port proximal to the balloon, the sleeve being affixed to the balloon, the sleeve extending through the sleeve lumen and the distal end of the sleeve being affixed within the sleeve lumen.

16. A catheter according to claim 14 wherein the core wire extends approximately 1.0 to 2.0 mm distal to the balloon distal cone.

17. A catheter according to claim 14 wherein the tube is made of irradiated thermoplastic.

18. A catheter according to claim 14 wherein the core wire extends a minimum of 0.5 mm into the compressed area, and not exceeding the length of the compressed area.

19. A catheter according to claim 14 wherein the compressed area extends a minimum of 0.5 mm.

20. A catheter according to claim 14 wherein at least one marker band having a proximal end and a distal end is affixed to the core wire within the balloon, wherein the proximal end of the tube extends distal to the distal end of the marker band.

* * * * *

UNITED STATES PATENT AND TRADEMARK OFFICE
CERTIFICATE OF CORRECTION

PATENT NO. : 5,458,639
DATED : October 17, 1995
INVENTOR(S) : Ross Tsukashima; Karen M. Rowean; Morris Deitermann It is certified that error appears in the above-indentified patent and that said Letters Patent is hereby corrected as shown below:

Column 6, Line 65, "preening" should be --preceding--.

Inventors: Dietermann should be spelled --Deitermann--.

Signed and Sealed this

Thirty-first Day of December, 1996

Attest:

BRUCE LEHMAN

Attesting Officer    Commissioner of Patents and Trademarks